(12) United States Patent
Bigdeli-Issazadeh et al.

(10) Patent No.: US 7,901,410 B2
(45) Date of Patent: Mar. 8, 2011

(54) COUPLING SYSTEM FOR AN INTRAMEDULLARY NAIL AND ASSOCIATED INSTRUMENTS

(75) Inventors: Sabine Bigdeli-Issazadeh, Felde (DE); Axel Cremer, Fahrenkrog (DE)

(73) Assignee: Stryker Trauma GmbH (DE)

( * ) Notice: Subject to any disclaimer, the term of this patent is extended or adjusted under 35 U.S.C. 154(b) by 1816 days.

(21) Appl. No.: 10/864,039

(22) Filed: Jun. 9, 2004

(65) Prior Publication Data

US 2005/0004600 A1   Jan. 6, 2005

(30) Foreign Application Priority Data

Jun. 11, 2003 (DE) ................ 203 09 058 U (51) Int. Cl.
*A61B 17/58* (2006.01)
*A61B 17/60* (2006.01)
*F16B 21/02* (2006.01)
*F16B 7/20* (2006.01)
*B25G 3/16* (2006.01)

(52) U.S. Cl. ............. 606/98; 606/62; 606/63; 606/64; 606/96; 606/97; 606/99; 403/348; 403/349; 403/350; 403/351; 403/352; 403/353

(58) Field of Classification Search ............ 606/62–64, 606/96–99; 403/348–353
See application file for complete search history.

(56) References Cited

U.S. PATENT DOCUMENTS

| | | | | |
|---|---|---|---|---|
| 959,226 A * | 5/1910 | Keys | ................... | 285/87 |
| 2,444,758 A * | 7/1948 | Stillbach | ................. | 403/349 |
| 2,672,861 A * | 3/1954 | Jonas et al. | .............. | 606/63 |
| 3,478,302 A * | 11/1969 | Chirumbolo | ............. | 403/349 |
| 4,487,469 A * | 12/1984 | Bjork | ................. | 439/332 |
| 4,943,182 A * | 7/1990 | Hoblingre | ............. | 403/349 |
| 5,156,483 A * | 10/1992 | Mangas | .............. | 403/288 |
| 5,176,681 A | 1/1993 | Lawes et al. | | |
| 5,308,350 A * | 5/1994 | Mikhail | ............ | 606/88 |
| 5,499,986 A | 3/1996 | Dimarco | | |
| 6,010,508 A | 1/2000 | Bradley | | |
| 6,022,355 A * | 2/2000 | Peche et al. | ............ | 606/93 |

(Continued)

FOREIGN PATENT DOCUMENTS

DE        2246274 A  *  3/1974

(Continued)

*Primary Examiner* — Thomas C Barrett
*Assistant Examiner* — Sameh Boles
(74) *Attorney, Agent, or Firm* — Lerner, David, Littenberg, Krumholz & Mentlik, LLP (57) ABSTRACT

An intramedullary nail and a targeting and/or nailing instrument includes a connector end which has an axially parallel projection which cooperates with an axially parallel recess on the hollow connection end of the nail. The engagement of the projection and recess fastens the nail under axial engagement on the connection end of the instrument in predefined rotational position on the instrument. A quick-fastener element engages in the connection end of the nail and has a first coupling element and the connection end of the nail has a second coupling element. The coupling elements are configured so that in a first rotational position relative to the axially parallel projection the instrument can be introduced into the connection end of the nail and in a second rotational position the coupling elements cooperate so that the nail is held axially fixedly on the instrument.

11 Claims, 5 Drawing Sheets

U.S. PATENT DOCUMENTS

| | | | |
|---|---|---|---|
| 6,183,477 B1 * | 2/2001 | Pepper | 606/104 |
| 7,175,633 B2 * | 2/2007 | Roth et al. | 606/99 |
| 7,296,804 B2 * | 11/2007 | Lechot et al. | 606/62 |
| 7,338,497 B2 * | 3/2008 | Coon et al. | 606/99 |
| 7,344,565 B2 * | 3/2008 | Seyer et al. | 623/22.21 |
| 2005/0203520 A1 * | 9/2005 | Volzow | 606/62 |

FOREIGN PATENT DOCUMENTS

| | | |
|---|---|---|
| DE | 19806323 | 2/1998 |
| EP | 0441256 | 2/1991 |
| WO | 03/041595 | 11/2002 |

\* cited by examiner

COUPLING SYSTEM FOR AN INTRAMEDULLARY NAIL AND ASSOCIATED INSTRUMENTS

BACKGROUND OF THE INVENTION

The invention relates to a combination comprised of an intramedullary nail and a targeting and/or nailing instrument. More particularly, it relates to a coupling system for quickly connecting an instrument to a bone nail.

Intramedullary nails are generally driven into the intramedullary space using a so-called nailing instrument. The nailing instrument is connected using a suitable connection with the nail before the nail is driven into the bone with the aid of a hammer or the like. In the case of so-called locking nails, which are provided with transverse bore holes for receiving bone or locking screws, a targeting instrument serves also as the nailing instrument. The targeting instrument is connected with the facing end of the bone nail using a clip and a targeting section running parallel to the bone is used for locating the otherwise invisible transverse bore holes of the nail in the bone. For this reason, it is necessary to orient the nail and the targeting device in a predefined rotational position relative to each other. To this end, it is well-known to provide an axially parallel projection at the connection end of the targeting device, which engages in an axially parallel recess. The connection of the connection end of the targeting device with the nail is generally done with the aid of a screw or by using a screw sleeve as disclosed in U.S. Pat. No. 5,176,681. The screw sleeve is used to keep a passage open to the inside of the nail, so that it is possible to introduce or to actuate a locking screw in the nail, while the targeting device is connected with the nail. The locking screw is used to lock a femoral neck screw, which is passed through an inclined transverse bore hole of the nail. The locking screw prevents movement of the neck screw in particular in the direction of rotation, but allows axial movement of the neck screw.

The known system requires setting the nail on the targeting unit manually and at the same time screwing the parts together which is relatively cumbersome for one person acting alone.

SUMMARY OF THE INVENTION

Therefore, one aspect of the invention is to simplify handling of the connection between the nail and the targeting and/or nailing instrument.

In the case of the present invention this aspect is achieved with a quick-fastener element rotationally mounted on the connection end of the targeting and/or nailing instrument. The element engages in the hollow connection end of the nail and has a first coupling element. The connection end of the nail has on its inside a second coupling element and the coupling elements are configured, so that in a first rotational position of the quick-fastener element, in which the quick-fastener element has a relative rotational position via-à-vis an axially parallel projection, into which the connection end of the nail can be introduced in a second rotational position of the quick-fastener element. The coupling elements cooperate for holding the nail axially fixed on the targeting and nailing instrument.

When bringing together the nail and the targeting and/or nailing instrument, the nail is on the one hand positioned opposite to the instrument in the correct rotational position, so that the axially parallel projection can engage in an axially parallel recess of the nail. At the same time, the quick-fastener element is rotated into a position, in which it can be introduced into the open end of the nail. Then the quick-fastener element is rotated into its second position, whereby the coupling elements interlock with each other, in order to establish an axial fixation of the nail on the targeting nailing instrument. Rotational fixation is already accomplished virtue of the interlocking of the axially parallel projection of the connection end of the instrument in the axially parallel recess of the nail.

The embodiment according to the invention has the advantage, that fixation of a nail, the targeting and nailing instrument and also the removal thereof is considerably simplified. It is necessary that the nail is appropriately configured at the connection end, whereby a coupling element is created, which cooperates with the coupling element of the quick-fastener element.

Manipulation in the case of the invention is even improved more, if the quick-fastener element is spring biased in the first rotational position towards the second rotational position. The first and second coupling elements are configured, so that they automatically cooperate, when the quick-fastener element is installed axially in the connection end of the nail in a predefined section.

One possible embodiment of the coupling element in the nail resides in that a threaded section is provided in the nail. Further, at least one axially parallel groove is formed in the nail, with which a radial projection of the quick-fastener element cooperates. The projection is introduced into the axially parallel groove of the nail by a predefined distance and then upon rotation of the quick-fastener element cooperates with a thread segment or a groove of the threaded segment. Obviously, the pitch of the threaded segment in the nail is extremely low because the quick-fastener element is mounted preferably axially fixed in the connection end of the targeting and/or nailing instrument. Preferably, three radial projections arranged in 120° intervals are provided on the quick-fastener element, said projections being spaced axially around the thread pitch. The threaded and grooved segment is then so configured that one projection each cooperate with one lead segment of the threaded segment.

According to one embodiment of the invention, the quick-fastener element has a sleeve, which is axially fixedly but limitedly rotatably mounted in a bore hole of the connection end of the targeting and nailing instrument. The sleeve has a radial actuating pin, which extends outwardly through a radial slot in the connection end. It is, in fact conceivable, to use also a cylindrical body as the quick-fastener element instead of a sleeve. The sleeve has the advantage, that using the sleeve, access to the inside of the nail is preserved, for actuation of a locking pin in the nail.

It has already been mentioned that the quick-fastener element can be biased in the direction of rotation. According to one embodiment of the invention, the spring for pre-tensioning the quick-fastener element is a helical spring, which cooperates on the one hand with the sleeve and on the other with the bore hole of the connection end of the instrument.

In order to make possible a reliable contact of the targeting and nailing instrument at the nail, it is advantageous according to a further embodiment of the invention, if the connection end of the targeting and nailing instrument has a sleeve-like end section, which approximately fittingly engages in a corresponding bore hole segment of the connection end of the nail.

These and other aspects of the invention are achieved by a connection system for coupling an instrument to a bone nail. This system includes a bone nail extending along a longitudinal axis and having a proximal end with an internal bore, including at least one slot extending parallel to the axis and at least one groove extending generally perpendicular to the axis intersecting the slot. The connector for coupling the instrument to the nail includes a spring-biased rotatable coupling element having an end for engaging the bore in the nail. The coupling element end includes at least one radially extending pin for engaging the at least one generally perpendicular groove. The coupling element is rotatable from a first position to a second position biased towards the first position wherein the pin on the coupling element is alignable with a slot in the nail in the second position after insertion in the nail end, and can engage the groove in the nail on movement from the second position towards the first position by action of the biasing spring. Preferably, the bone nail has three circumferentially spaced slots and three axially spaced grooves and the coupling element has three pins for respectively engaging the slots and grooves. In the preferred embodiment, the three slots and the three pins are circumferentially spaced at 120°. Also in the preferred embodiment, the coupling element is in the form of a rotatable sleeve mounted in a bore in the connector with a spring mounted between the bore in the connector and the sleeve for biasing the sleeve towards the first position. To facilitate movement of the sleeve within the bore of the connector, a radially extending actuator arm may be provided, which arm extends through a slot in the connector which allows movement of the sleeve from the first position to the second position so that the pins on the sleeves can be aligned with the slots in the end of the bone nail. In order to prevent the relative rotation of the connector and the nail end, an anti-rotation element such as an axial extension from the connector for engagement in the recess in a nail end is provided.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
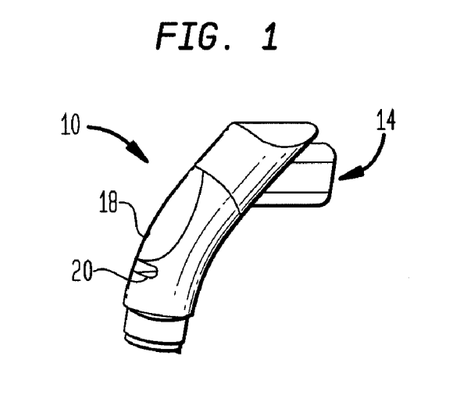
FIG. 1 is a perspective view of the connection end of a targeting and nailing instrument.
Figure 2:
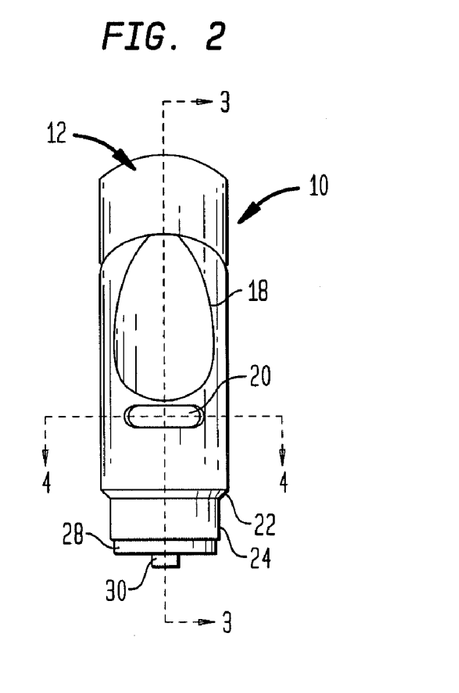
FIG. 2 is an enlarged lateral view of the instrument of FIG. 1.
Figure 3:
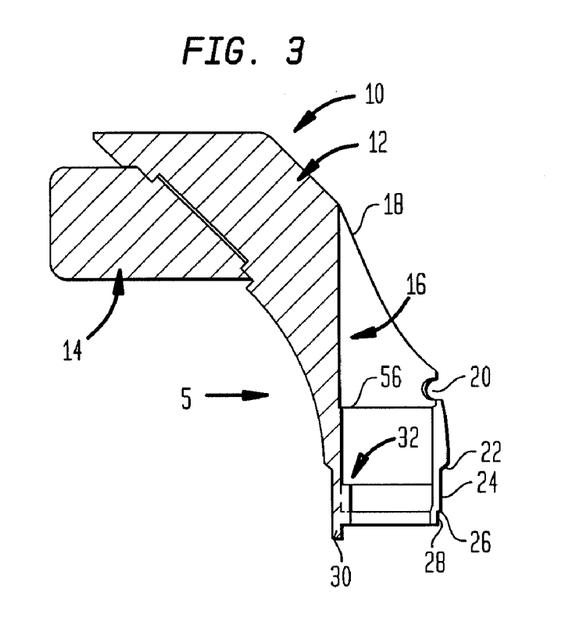
FIG. 3 is a sectional view through the instrument of FIG. 2 along the line 3-3.

FIGS. 1 to 3 represent a connection end 10 of a nailing and targeting instrument which has a targeting portion which is not represented in detail. Connection end 10 has a first part 12 and a second part 14 which, in the preferred embodiment, are bonded together by means of a weld. The part 14 serves as the connection with the other section of the targeting unit (not shown) and which is of no significance for the purposes of the description of the present invention.

Figure 4:
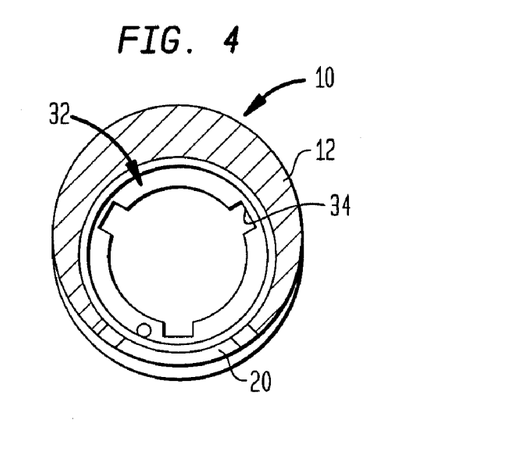
FIG. 4 is a sectional view through the instrument of FIG. 2 along the line 4-4.

In the preferred embodiment, the arcuate, deflected, circular cross-section part 12 has a straight linear bore hole 16, which opens upwardly into an inclined opening 18. A short distance below the opening 18 a radial slot 20 is formed in the part 12; a conical step 22 is situated underneath the slot 20 and step 22 is a cylindrical section 24. The cylindrical section 24 transitions over a further radial step 26 into a cylindrical section 28 which has a smaller diameter than section 24. An axially parallel projection 30 connects to section 28. On the inside of the bore hole 16, at the level of the cylindrical section 24, there is a radial flange 32 oriented inwardly, which, as can be seen in FIG. 4 has three radial recesses 34 arranged at 120° intervals.

Figure 5:
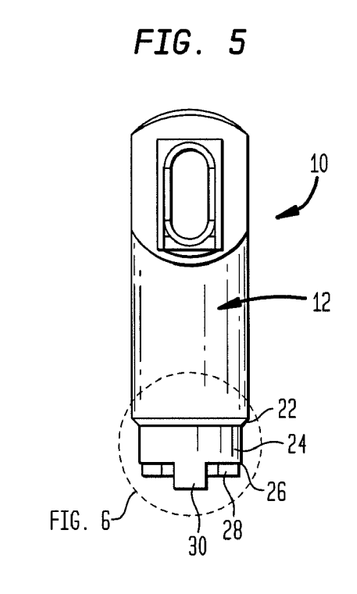
FIG. 5 is a lateral view of the instrument viewed from arrow 5 of FIG. 3.
Figure 6:
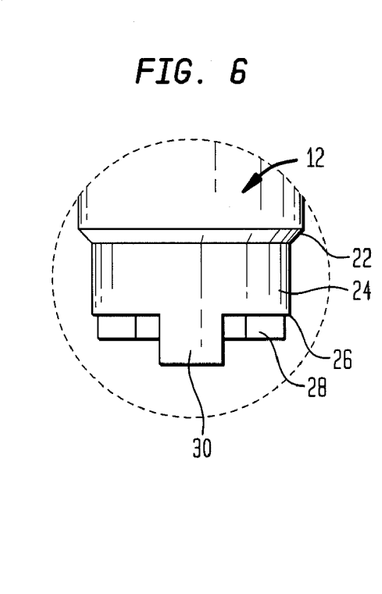
FIG. 6 is an enlargement of the area of FIG. 5 in circle 6.
Figure 7:
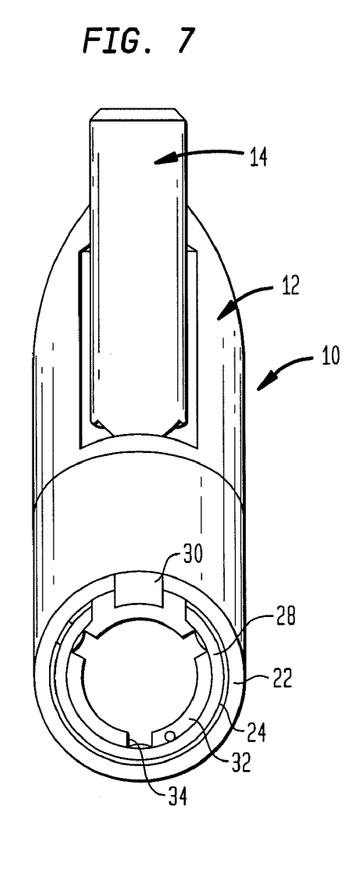
FIG. 7 is a bottom view of the instrument according to FIG. 3 or FIG. 5.

FIGS. 5 and 7 show that the external diameter of the axially parallel projection 30 corresponds to the diameter of cylindrical section 24. In the preferred embodiment, section 28 ends on both sides of the projection 30 at a distance from the projection (as can be seen especially in FIG. 7).

Figure 12:
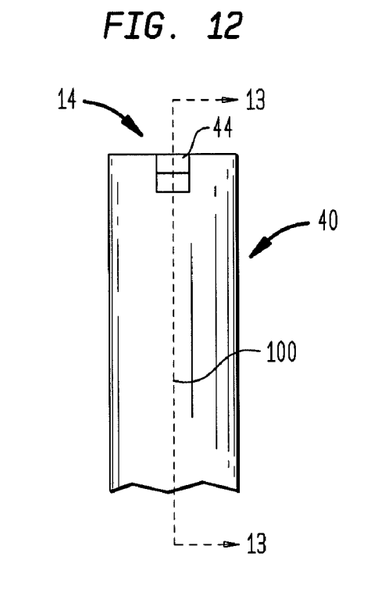
FIG. 12 is the connection end of a locking nail (partially shown)

In the preferred embodiment, an upper nail section 40 is shown in FIGS. 12 to 15. It is part of a cylindrical nail shaft, which has an axial bore hole 42. As can be seen in FIG. 12, the nail section 40 has a recess 44 parallel to the nail axis 100 at its upper end. The bore hole 42 has an upper enlarged portion 43 and at the upper end a bore hole section 46 is provided. The internal diameter of the bore hole section 46 corresponds to the external diameter of cylindrical section 28 of the connection end of the instrument 10. The connection end can therefore be inserted with the section 28 into the bore hole section 46, wherein the axially parallel projection 30 engages appropriately in the recess 44. In the preferred embodiment, the external diameter of nail section 40 corresponds to the external diameter of section 24 of the connection end of instrument 10.

Figure 8:
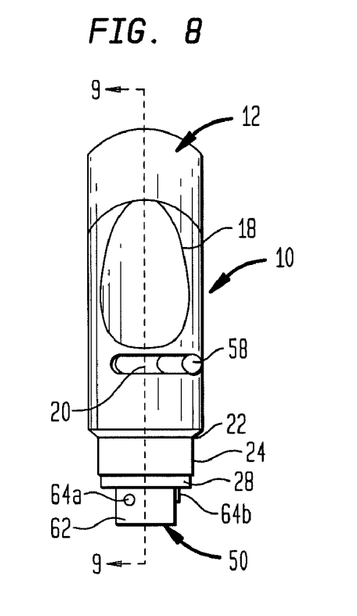
FIG. 8 is a view similar to that of FIG. 2 but with an installed quick-fastener element.
Figure 9:
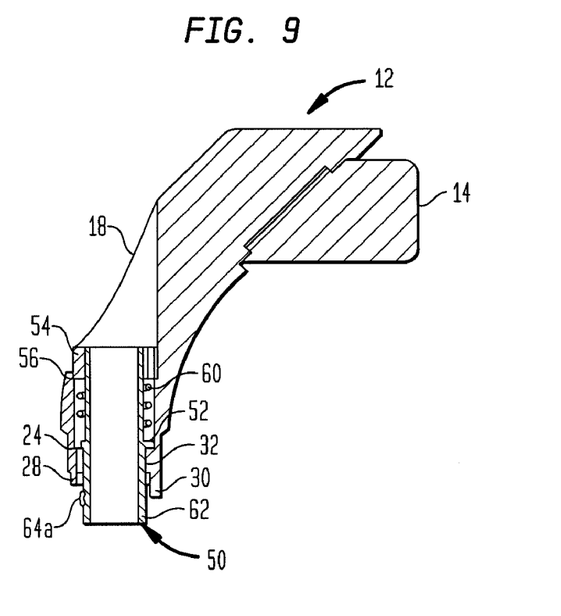
FIG. 9 is a sectional view through FIG. 8 along line 9-9.

FIGS. 8 to 11 show a quick-fastener inserted into the connection end of the instrument. The preferred quick-fastener is a sleeve 50, which is inserted into the bore hole 16 of the part 12. Sleeve 50 has a radial flange 52, which cooperates with a collar which is formed by the radial flange 32. In the axial space above radial flange 52, sleeve 50 has at its upper left end (as shown in FIG. 9) a further radial flange 54, which can engage a recessed surface 56 for attachment. An actuation pin 58 is compressed radially in a bore hole 55 of the flange 54. Pin 58 extends through the radial slot 20. An annular space in which a helical spring 60 is arranged is formed between sleeve 50 and the bore hole section between the recess 56 and the flange 32. The one end of the helical spring is fixedly connected to the part 12 and the other end is connected to the sleeve 50. A rotation of sleeve 50 therefore results in a pretensioning of sleeve 50 by spring 60.

Figure 11:
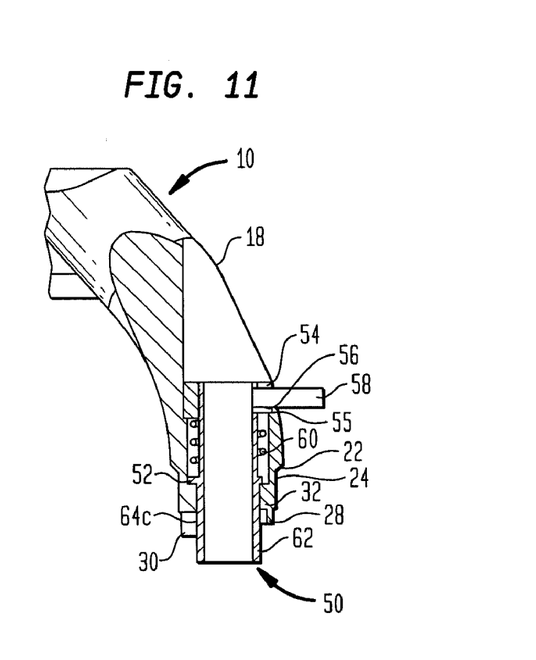
FIG. 11 is a sectional view through FIG. 10 along the line 11-11.

As can be seen in FIGS. 8, 9 and 11, in the installed position, the sleeve 50 projects downwardly. As can be seen further in these figures, the overhanging sleeve section 62 is provided with short radial studs 64. In total, in the preferred embodiment, three studs 64 are arranged in peripheral intervals of 120° and are preferably axially spaced as well. This spacing will be explained in more detail below.

Figure 13:
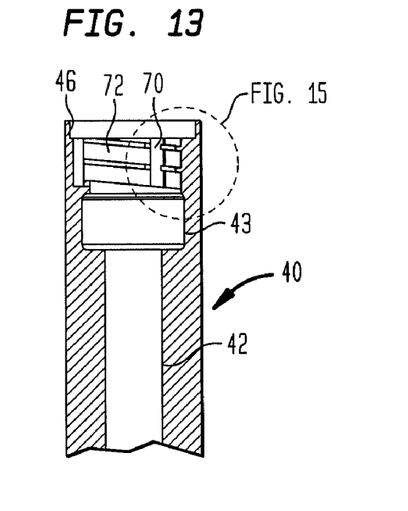
FIG. 13 is a sectional view through the nail according to FIG. 12 along the line 13-13.
Figure 14:
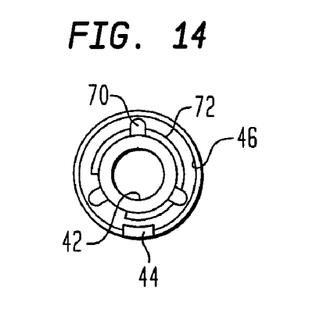
FIG. 14 is an end view of the nail according to FIG. 12 in the direction of the arrow 14.
Figure 15:
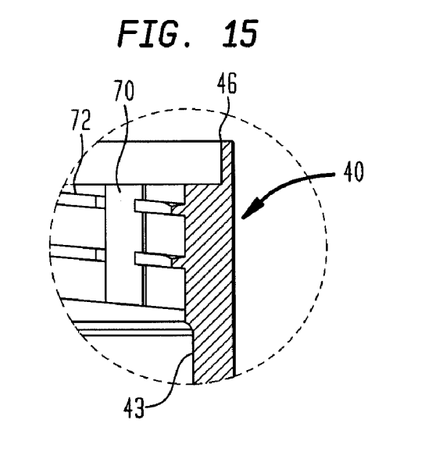
FIG. 15 represents an enlargement of area 14 according to FIG. 13.

It can be clearly seen in FIGS. 13 to 15, that below bore hole section 46 three axially parallel grooves are formed in the wall of the nail section 40. These are indicated by reference 70. Grooves 70 interrupt a thread section 72, which is formed below bore hole section 46. The pitch of this thread is extraordinarily flat. Each groove 70 cooperates with a pin 64 upon assembly of nail 40 and connection end 10.

Figure 10:
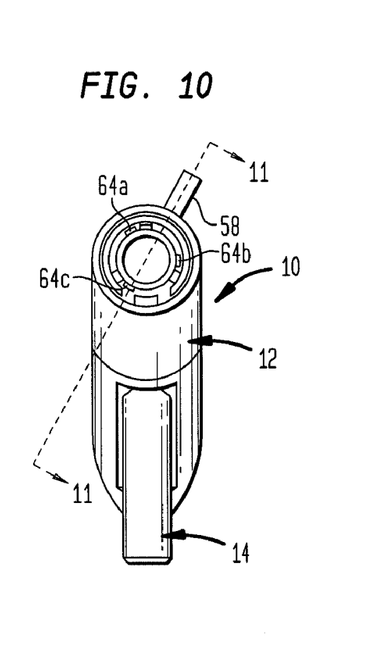
FIG. 10 is a top view of the instrument of FIG. 8 or 9.
Figure 16:
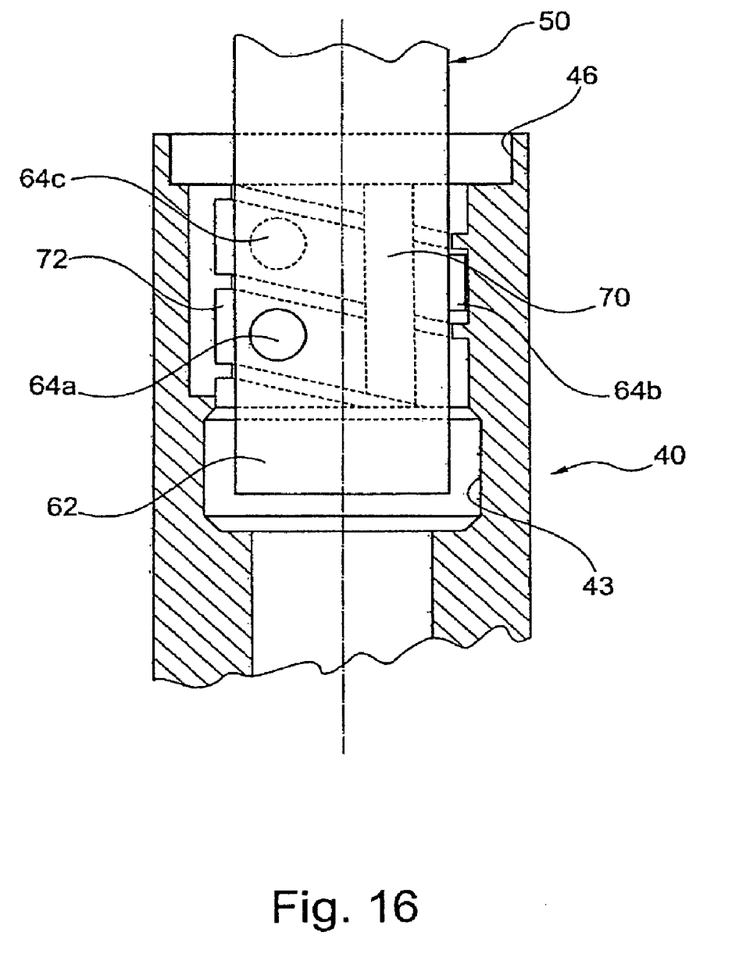
FIG. 16 is a partial cross-sectional view of the sleeve shown in FIGS. 8 and 9 inserted into the nail end of FIGS. 13 and 15.

As can be seen in FIG. 10, the three radial projections or studs 64*a, b* and *c* are oriented at 120° and are axially offset around the threaded circumference of nail end portion 43 as shown in FIG. 16.

If, as described above, connection end 10 is inserted into nail section 40, in which cylindrical section 28 engages in bore hole section 46 and projection 30 in the recess 44, then this can be accomplished only if, in addition, sleeve 50 has a rotational position, so that one stud 64 can be introduced in to each groove 70. In order to achieve this rotational positioning, sleeve 50 must be correspondingly rotated; that is, with the aid of actuation pin 58. With this rotation, the helical spring 60 is tensioned. If, in the described arrangement of the parts, the nail is completely pushed in using part 12 of the connection end 10, the pins 64 are oriented towards a thread lead of the thread section 72 or towards a thread groove. The axial spacing of studs 64 is such, that it corresponds to the pitch of thread section 72. If now, in the described arrangement of the parts, actuation pin 58 is released, the sleeve 50 is urged by the spring 60 to rotate back into the unstressed or less stressed position, whereby the studs 64 engage into each one groove section of the thread section 72 and thereby establish a locking with the nail section 40. In this fashion, the nail section 40 is affixed both in the direction of rotation and axially securing to the connection end 10 of the instruments.

An alternative attachment of the nail section 40 to the instrument 10 is done as follows. The nail end 40 is pushed over the projecting sleeve section 62, whereby the studs 64 engage in the grooves or slots 70. Then the nail section 40 is rotated relative to the instrument 10, until the projection 30 is aligned with the recess 44 of the nail section. After this alignment, the nail is pushed farther forward against the instrument 10, so that the projection 30 engages completely in the recess 40. As soon as this is completed, the studs 64 are in alignment with the groove sections of the thread section 72 and move automatically into same, because with the described rotating the helical spring 60 was pre-stressed and attempts to rotate the sleeve 50 back into the unrotated direction.

This explanation makes clear that in the described figures a quick-fastener is shown with which the nail, a locking nail, for example, can be connected using a targeting and/or nailing instrument quickly without the assistance of instruments or a screw or the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A combination comprising an intramedullary nail and a nailing instrument connecting to a proximal end of the nail, wherein the nailing instrument has a bore extending along an axis directed towards the nail, the bore having an inclined opening inclined towards the axis on moving away from an outer surface of the nailing instrument from the proximal end of the nail, and a radial slot extending perpendicular to the axis from an inner surface of the bore to the outer surface of the nailing instrument, the radial slot located on the outer surface between an end of the inclined bore and a connecting end of the nailing instrument, the connecting end of the nailing instrument has an axially parallel projection, which cooperates with an axially parallel recess on a hollow connection end of the nail, in order to fasten the nail under axial engagement on the connection end of the nailing instrument in predefined rotational position, the nailing instrument further comprising a quick-fastener element having radially outwardly extending projections rotationally mounted on the connection end of the nailing instrument which engages the connection end of the nail and the quick-fastener element and nail each having coupling means, the coupling means configured so that in a first rotational position of the quick-fastener element the quick-fastener element has a rotational position relative to the axially parallel projection and can be introduced into the connection end of the nail and in a second rotational position of the quick-fastener element, the coupling means of the quick-fastener element and nail cooperate, so that the nail is held axially fixedly on the nailing instrument wherein the quick-fastener element is pre-stressed in the first rotational position by a spring acting thereon and the coupling means are configured so that they automatically cooperate when the quick-fastener has been introduced by a predefined distance axially into the connection end of the nail wherein the connection end of the nail has an internal threaded section with three axially parallel grooves, the quick-fastener element has three radial projections one of which can be introduced into each axially parallel groove and upon rotation of the quick-fastener element from the first into the second rotational position cooperates with a lead section of the thread section wherein the three radial projections are arranged in 120° spacing and are axially offset from each other around a thread pitch and the inside of the axially parallel grooves are offset at 120° wherein the thread section is configured so that each radial projection cooperates with one lead section of the thread section wherein the quick-fastener element is a sleeve which is axially fixed but rotatable in a bore hole of the connection end of the nailing instrument and the sleeve further comprised a radial actuating pin which projects outwardly through the radial slot of the nailing instrument allowing a user to rotate the sleeve against the spring.

2. The combination as set forth in claim 1 wherein a helical spring is arranged in space between the sleeve and wall of the bore hole in the connection end of the targeting and/or nailing element, the one end of said helical spring being fastened to the connection end and the other end being fastened to the sleeve.

3. The combination as set forth in claim 1 wherein the sleeve has a first radial flange which abuts against a radial counter surface in the bore hole of the connection end and the sleeve is axially fastened by means of the actuation pin in the opposite direction whereby the spring under axial pre-stressing abuts against the flange of the sleeve and against the actuation pin or against another radial flange carrying the actuation pin.

4. The combination as set forth in claim 1 wherein the connection end of the nailing instrument has a sleeve-like end section which fittingly engages in a terminal bore hole section of the connection end of the nail.

5. The combination as set forth in claim 4 wherein the axially parallel projection of the connection end of the nailing instrument axially overhangs the free end of the sleeve-like end section.

6. A connection system for coupling a nailing instrument to a bone nail, the system comprising:

a bone nail extending along a longitudinal axis and having a proximal end with an internal bore including three slots extending parallel to said axis and three axially spaced grooves, each axially spaced groove extending in a direction generally perpendicular to said axis and each groove intersecting one of the slots at a different axial location thereon; and a nailing instrument for coupling to a proximal end of the nail, the nailing instrument having a bore extending along an axis directed towards the nail, the bore having an inclined opening inclined towards the axis on moving away from an outer surface of the nailing instrument from the proximal end of the nail, and a radial slot extending perpendicular to the axis from an inner surface of the bore to the outer surface of the nailing instrument, the radial slot located on the outer surface between an end of the inclined opening, the nailing instrument having a connector for coupling the instrument to the nail, the connector comprising a spring-biased rotatable coupling element having an end for engaging said bore in said bone nail, said coupling element end including three axially spaced radially extending pins each for engaging one of the axially spaced grooves, said coupling element rotatable from a first position to a second position and being biased towards said first position, wherein one of said pins is alignable with each of said slots in said second position and can engage said axially spaced grooves on movement from said second position towards said first position, wherein the coupling element is in the form of a rotatable hollow sleeve mounted in the nailing instrument bore and a spring mounted between said bore and said sleeve biases said sleeve towards said first position, the sleeve further comprising a radial actuating pin extending through the radial slot to allow a user to rotate the sleeve against the spring.

7. The connection system as set forth in claim 6 wherein said three slots and said three pins are circumferentially spaced at 120°.

8. The connection system as set forth in claim 6 wherein said coupling element and the first nail end include operatively engageable anti-rotation means.

9. A connection system for coupling a nailing instrument to a bone nail, the system comprising:

a bone nail extending along a first longitudinal axis and having a proximal end with an internal bore including at least one slot extending parallel to the first longitudinal axis and at least one groove extending generally in a plane perpendicular to the longitudinal axis intersecting said slot; and a nailing instrument for coupling to a proximal end of the nail, the nailing instrument having a bore extending along an axis directed towards the nail, the bore having an inclined opening inclined towards the axis on moving away from an outer surface of the nailing instrument from the proximal end of the nail, and a radial slot extending perpendicular to the axis from an inner surface of the bore to the outer surface of the nailing instrument, the radial slot located on the outer surface between an end of the inclined opening, the nailing instrument having a connector for coupling the instrument to the nail, the connector comprising a spring-biased rotatable coupling element having an end for engaging said bore in said bone nail, said coupling element end including at least one radially extending pin for engaging said at least one groove, said coupling element rotatable from a first position to a second position and spring-biased towards said first position, wherein said pin is alignable with said slot in said second position and can engage an end of said groove on spring-biased movement from said second position towards said first position, the coupling element being in the form of a rotatable sleeve mounted in the bore and a spring mounted between the bore and the sleeve biases the sleeve towards the first position wherein the sleeve further comprises a radially extending actuating pin for extending through the radial slot allowing a user to move the sleeve from the first position to the second position against the spring.

10. The connection system as set forth in claim 9 wherein said bone nail bore has three circumferentially spaced slots and three axially spaced grooves and said coupling element has three axially and circumferentially spaced pins for respectively engaging said slots and grooves.

11. The connection system as set forth in claim 10 wherein said three slots and said three pins are circumferentially spaced at 120°.

\* \* \* \* \*